(12) United States Patent
Iceman et al.

(10) Patent No.: US 10,682,187 B2
(45) Date of Patent: Jun. 16, 2020

(54) SURGICAL ROBOTIC CART IMMOBILIZER

(71) Applicant: Covidien LP, Mansfield, MA (US)

(72) Inventors: Jason Iceman, Cheshire, CT (US); James Lattimore, Fairport, NY (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/173,560

(22) Filed: Oct. 29, 2018

(65) Prior Publication Data
US 2019/0060005 A1  Feb. 28, 2019

Related U.S. Application Data

(63) Continuation of application No. 15/552,853, filed as application No. PCT/US2016/021509 on Mar. 9, 2016, now Pat. No. 10,123,842.

(60) Provisional application No. 62/131,558, filed on Mar. 11, 2015.

(51) Int. Cl.
| A61B 34/20 | (2016.01) |
| B25J 5/00 | (2006.01) |
| A61B 90/50 | (2016.01) |
| A61B 34/30 | (2016.01) |
| B60B 33/00 | (2006.01) |
| A61B 50/13 | (2016.01) |

(52) U.S. Cl.
CPC .............. *A61B 34/20* (2016.02); *A61B 34/30* (2016.02); *A61B 90/50* (2016.02); *B25J 5/007* (2013.01); *B60B 33/0089* (2013.01); *A61B 50/13* (2016.02); *A61B 2090/508* (2016.02)

(58) Field of Classification Search
CPC ......... A61B 34/20; A61B 34/30; A61B 50/13; A61B 90/50; A61B 2090/508; B25J 5/007; B60B 33/0089
See application file for complete search history.

(56) References Cited

U.S. PATENT DOCUMENTS

| 4,339,842 A * | 7/1982 | Fontana .............. B60B 33/0042 16/32 |
| 4,593,883 A | 6/1986 | Nelson |

(Continued)

FOREIGN PATENT DOCUMENTS

| CN | 202278381 U | 6/2012 |
| CN | 103963646 A | 8/2014 |
| DE | 202012007320 U1 | 8/2012 |

OTHER PUBLICATIONS

Extended European Search Report corresponding to counterpart Patent Application EP 16762402.2 dated Feb. 18, 2019.

(Continued)

*Primary Examiner* — Erez Gurari

(57) ABSTRACT

A mobile surgical robotic cart assembly used for minimally invasive surgery includes a vertical column supporting a robotic arm thereon and a base portion having at least three casters adapted to allow the surgical robotic assembly to move. The surgical robotic cart assembly further includes an immobilization assembly coupled to the base portion, the immobilization assembly being configured to move between an unlocked position and a locked position. The surgical robotic cart assembly is mobile when the immobilization assembly is in the unlocked position and immobile when the when the immobilization assembly is in the locked position.

19 Claims, 9 Drawing Sheets

(56) References Cited

U.S. PATENT DOCUMENTS

| | | | | |
|---|---|---|---|---|
| 5,042,110 | A * | 8/1991 | Orii | B60B 33/0042 16/32 |
| 5,323,879 | A * | 6/1994 | Poulin | B62B 5/049 188/19 |
| 6,637,071 | B2 * | 10/2003 | Sorensen | B60B 33/0002 16/19 |
| 7,216,399 | B2 * | 5/2007 | Webster | B62B 5/049 16/32 |
| 8,136,201 | B2 * | 3/2012 | Yantis | A47B 91/022 16/18 R |
| 8,365,353 | B2 * | 2/2013 | Block | B60B 33/0007 16/35 R |
| 8,753,009 | B2 * | 6/2014 | Gregerson | A61B 6/035 378/196 |
| 9,771,092 | B2 * | 9/2017 | Johnson | B62B 3/10 |
| 10,071,488 | B2 * | 9/2018 | Robinson | B25J 5/007 |
| 10,123,842 | B2 * | 11/2018 | Iceman | B25J 5/007 |
| 2005/0154431 | A1 | 7/2005 | Quistgaard et al. | |
| 2006/0010643 | A1 * | 1/2006 | Hornbach | B60B 33/0018 16/19 |
| 2006/0082088 | A1 | 4/2006 | Webster et al. | |
| 2011/0247173 | A1 * | 10/2011 | Nguyen | B60B 7/00 16/45 |
| 2011/0247903 | A1 * | 10/2011 | Boukhny | B60B 33/0042 188/68 |
| 2014/0052153 | A1 * | 2/2014 | Griffiths | A61B 34/70 606/130 |
| 2014/0076659 | A1 * | 3/2014 | Terry | A47L 3/02 182/13 |
| 2014/0297130 | A1 * | 10/2014 | Griffiths | B25J 5/007 701/42 |
| 2015/0374446 | A1 * | 12/2015 | Malackowski | A61B 34/32 606/130 |
| 2017/0087730 | A1 * | 3/2017 | Robinson | A61B 34/35 |
| 2017/0151021 | A1 * | 6/2017 | Quaid, III | A61B 17/3403 |
| 2017/0333145 | A1 * | 11/2017 | Griffiths | A61B 34/30 |
| 2017/0360517 | A1 * | 12/2017 | Crawford | A61B 17/025 |
| 2017/0361461 | A1 * | 12/2017 | Tan | B25J 5/00 |
| 2018/0042682 | A1 * | 2/2018 | Iceman | B25J 5/007 |
| 2018/0071026 | A1 * | 3/2018 | Malackowski | A61B 34/32 |

OTHER PUBLICATIONS

Chinese First Office Action dated Aug. 26, 2019 corresponding to counterpart Patent Application CN 201680014660.2.

International Search Report for (PCT/US2016/021509) date of completion is May 20, 2016 (3 pages).

Partial Supplementary European Search Report corresponding to counterpart Patent Appln. EP 16762402.2 dated Nov. 6, 2018.

Australian Examination Report No. 1 dated Oct. 18, 2019 corresponding to counterpart Patent Application AU 2016229824.

* cited by examiner

SURGICAL ROBOTIC CART IMMOBILIZER

CROSS-REFERENCE TO RELATED APPLICATIONS

This application is a Continuation of U.S. patent application Ser. No. 15/552,853, filed on Aug. 23, 2017, which is a U.S. National Stage Application filed under 35 U.S.C. § 371(a) of International Patent Application Serial No. PCT/US2016/021509, filed Mar. 9, 2016, which claims the benefit of and priority to U.S. Provisional Patent Application Ser. No. 62/131,558, filed Mar. 11, 2015, the entire disclosure of each of which are incorporated by reference herein.

BACKGROUND

Surgical robotic systems are used in minimally invasive medical procedures because of their increased accuracy and expediency. In these surgical robotic systems, a robot arm supports a surgical instrument having an end effector mounted thereto by a wrist assembly. In operation, the robot arm inserts the surgical instrument into a small incision via a surgical portal or a natural orifice of a patient to position the end effector at a work site within a patient's body.

Most of the surgical robotic systems in the market are heavy and stationary requiring a pallet jack to be relocated. In some of the more modern surgical robotic systems, the robot arm is supported on a movable surgical robotic cart assembly having a base portion with a set of casters. This is beneficial because the surgical robotic systems can be moved between various rooms as needed.

However, minimally invasive medical procedures require a high amount of accuracy, precision, and speed, and, therefore, need to be immobilized before operation. Accordingly, there is a need to immobilize a surgical robotic cart assembly.

SUMMARY

The present disclosure is directed to a surgical robotic cart immobilizer for mobile surgical robotic systems to stabilize a surgical robotic system before operation.

In accordance with an embodiment of the present disclosure, a surgical robotic cart assembly includes a vertical column having a first end and a second end. The first end of the vertical column is configured to support a robotic arm thereon. The surgical robotic cart assembly also includes a base portion secured to the second end of the vertical column. At least three casters are attached to the base portion and adapted to allow the surgical robotic assembly to move. Attached to the base portion is an immobilization assembly having at least two pistons configured to move between an unlocked position and a locked position. When the at least two pistons are in the unlocked position the surgical robotic cart assembly is mobile, and when the at least two pistons are in the locked position and in contact with a floor on which the cart assembly is supported, the cart assembly is immobile.

The immobilization assembly may include a motor having a first motor shaft and a second motor shaft operatively coupled to the base portion, a first cam shaft supporting a first cam and a second cam shaft supporting a second cam. The first and second cam shafts are coupled to a respective one of the first and second motor shafts. The first cam housing and second cam housing each is attached to the base portion and is rotatably coupled to a respective one of the first and second cam shafts.

The first and second cams may be disposed within respective first and second cam housings. Each of the first and second cam housings may include a piston. Each of the pistons has a spring disposed around its circumference and is configured to hold each of the pistons in the unlocked position.

Each of the first and second cams of the first and second cam shafts may have a lobe shape defining a minimum radius and a maximum radius that is greater than the minimum radius.

At least a portion the first and second cams may be configured to engage a respective piston and spring of the first and second cam housings. When the at least one portion of the first and second cams having the minimum radius engages the respective piston and spring of the first and second cam housings, the pistons are in the unlocked position and the springs are in a released and uncompressed position. When the at least one portion of the first and second cams having the maximum radius engages the respective pistons and springs of the first and second cam housings, the pistons are in the locked position and the springs are in a compressed position.

The immobilization assembly may further include a third cam shaft. The third cam shaft is rotatably coupled to a third cam housing attached to the base portion and the third cam housing includes a respective piston fixed to a respective spring. The spring of the third cam housing is disposed around a circumference of the piston of the third cam housing and configured to hold the piston thereof in an unlocked position. At least one of the first or second cam shafts is operatively coupled to a third cam shaft.

The third cam shaft may support a third cam having a lobe shape defining a minimum radius and a maximum radius greater than the minimum radius.

At least a portion the third cam may be configured to engage the piston and spring of the third cam housing. When the at least one portion of third cam having the minimum radius engages the piston and spring of the third cam housing, the piston is in the unlocked position and the spring is in a released and uncompressed position. When the at least one portion of the third cam having the maximum radius engages the piston and spring of the third cam housing, the respective piston is in the locked position and the respective spring is in a compressed position.

A belt may operatively couple the third cam shaft to at least one of the first or second cam shafts.

A belt tensioner may be attached to the base portion and configured to apply a pressure to the belt to increase a tension thereof.

In accordance with another embodiment of the present disclosure, a surgical robotic cart assembly includes a vertical column having a first end and a second end. The first end of the vertical column is configured to support a robotic arm thereon. The surgical robotic cart assembly also includes a base portion secured to the second end of the vertical column. At least three casters are coupled to the base portion and adapted to allow the surgical robotic assembly to move. An immobilization assembly is coupled to the base portion, and includes at least three pistons configured to move between an unlocked position and a locked position. When the at least three pistons are in the unlocked position the surgical robotic cart assembly is mobile. When the at least three pistons are in the locked position and in contact with a floor on which the cart assembly is supported, the cart assembly is immobile.

The immobilization assembly may further include a first cam shaft supporting a first cam, a second cam shaft supporting a second cam, a third cam shaft supporting a third cam. The first, second, and third cam shafts are coupled to respective first, second, and third motors. The immobilization assembly may further include first, second, and third cam housings rotatably coupled to a respective one of the first, second, and third cam shafts. Each of the first, second, and third cam housings is attached to the base portion.

The first, second, and third cams may be disposed within a respective first, second, and third cam housing.

Each of the first, second, and third cam housings may include a piston. Each piston is coupled to a spring disposed around a circumference of the piston and configured to hold the piston in the unlocked position.

Each of the first, second, and third cams of the first, second, and third cam shafts may have a lobe shape defining a minimum radius and a maximum radius that is greater than the minimum radius.

At least a portion the first, second, and third cams may be configured to engage a respective piston and spring of the first, second, and third cam housings. When the at least one portion of the first, second, and third cams having the minimum radius engages the respective piston and spring of the first, second, and third cam housings, the pistons are in the unlocked position and the springs are in a released and uncompressed position. When the at least one portion of the first, second, and third cams having the maximum radius engages the respective pistons and springs of the first, second, and third cam housings, the pistons are in the locked position and the springs are in a compressed position.

In accordance with another embodiment of the present disclosure, a surgical robotic cart assembly includes a vertical column having a first end and a second end. The first end of the vertical column is configured to support a robotic arm thereon. The surgical robotic cart assembly also includes a base portion secured to the second end of the vertical column. At least three casters having an immobilization assembly are attached to the base portion. The immobilization assembly for each caster includes a housing, a threaded shaft having a first end and a second end. The first end of the threaded shaft is threadingly engaged with the housing. The threaded shaft is configured to translate from an unlocked position to a locked position. The surgical robotic cart assembly is mobile when the threaded shaft is in the unlocked position and immobile when the threaded shaft is in the locked position.

The immobilization assembly may further include a wing nut having a threaded interior surface for translating the threaded shaft relative to the housing. Rotating the wing nut moves the threaded shaft between the unlocked position and the locked position.

The immobilization assembly may further include a star knob having a threaded interior surface for translating the threaded shaft relative to the housing. Rotating the star knob moves the threaded shaft between the unlocked position and the locked position.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
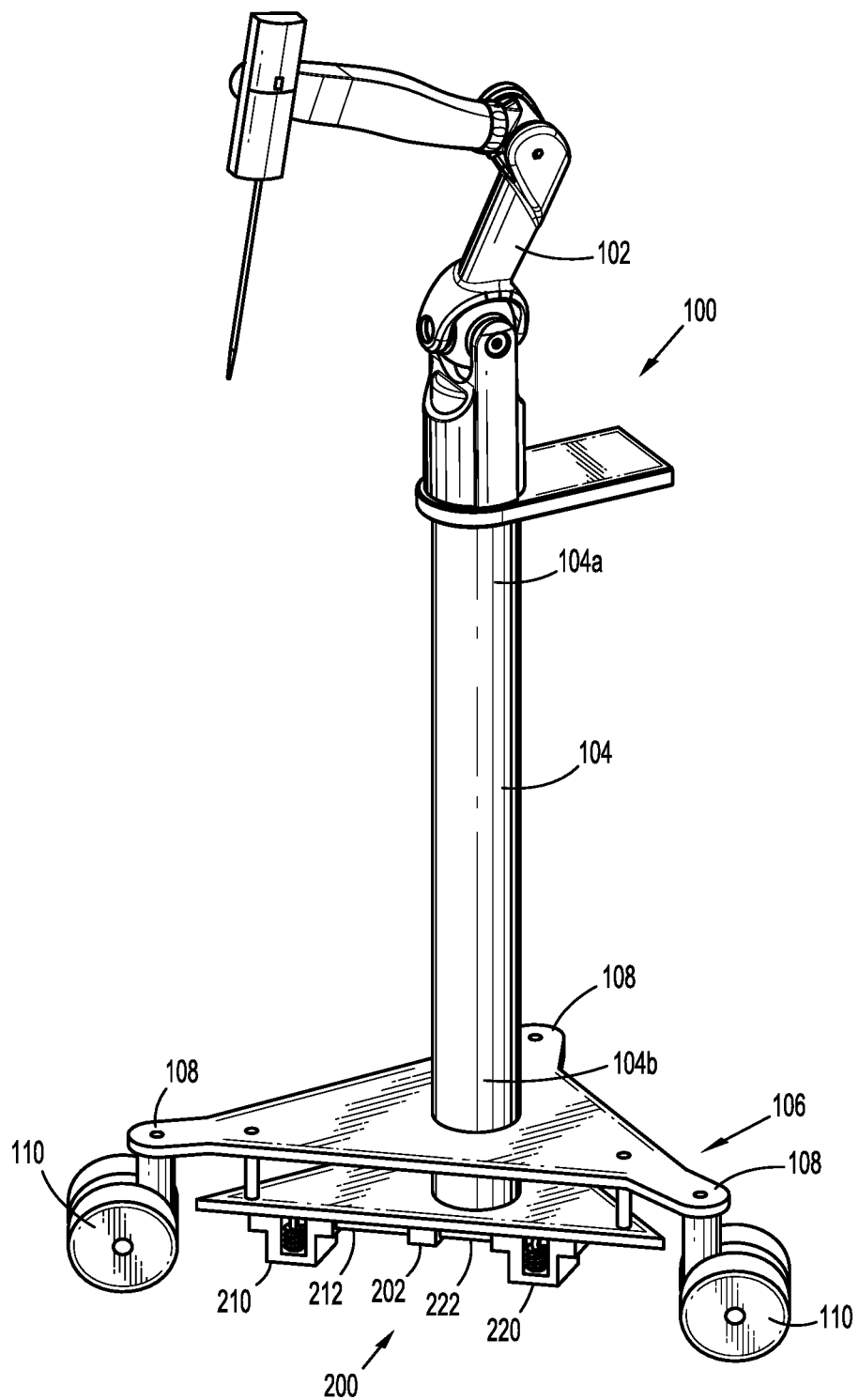
FIG. 1 is a perspective view of a surgical robotic cart having an immobilization assembly in accordance with the present disclosure.
Figure 2:
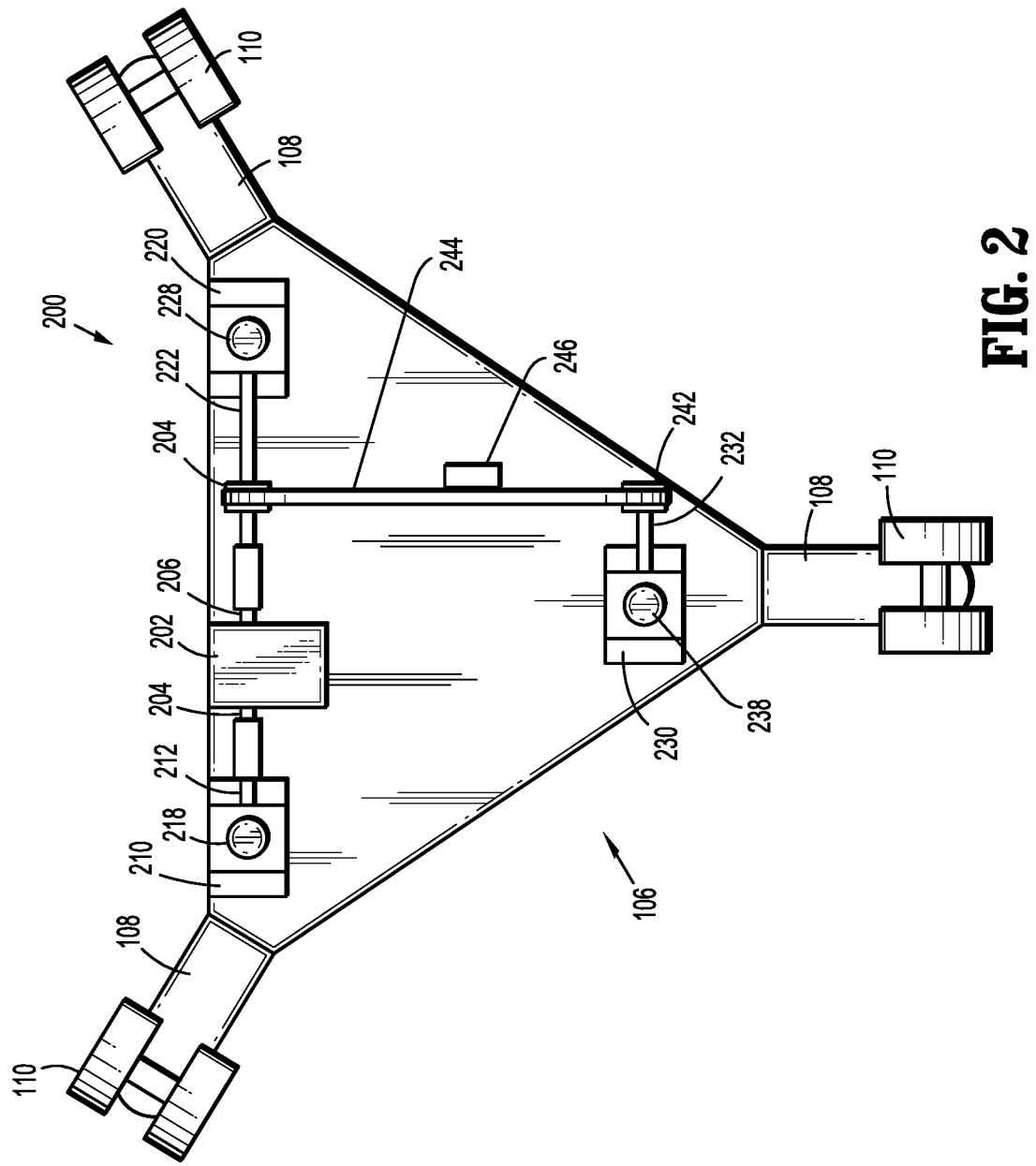
FIG. 2 is a plan, bottom view of the surgical robotic cart of FIG. 1.

Embodiments of the present disclosure are described in detail with reference to the drawings, in which like reference numerals designate identical or corresponding elements in each of the several views.

While surgical robotic systems are discussed below, only for brevity the features of the device disclosed herein will be directed towards surgical robotic systems. Surgical robotic systems use robotic arms having various gears, cams, pulleys, electric and mechanical motors to assist a surgeon in performing surgery and allows for remote operation (or partial remote operation) of the surgical instrumentation. Since these surgical robotic systems incorporate a large amount of hardware, they are typically heavy and stationary, requiring a pallet jack to move.

To address the immobility of surgical robotic systems, modern surgical robotic systems support the robotic arm on a surgical robotic cart assembly having a set of casters. This is beneficial because the surgical robotic systems can be relocated as needed or desired. However, mobile surgical robotic systems may not provide a requisite amount of immobility needed for a robotic surgical procedure. Therefore, a need exists to immobilize a surgical robotic system while it is in operation and mobilize the surgical robotic system while it is not in operation.

With reference to FIG. 1, one exemplary embodiment of a surgical robotic cart assembly configured for use in accordance with the present disclosure is shown generally as reference numeral 100, although it is also envisioned that the aspects and features of the present disclosure be similarly incorporated into any suitable surgical robotic cart assembly. Surgical robotic cart assembly 100 generally includes a robotic arm 102, a vertical column 104 having a first end 104a and a second end 104b, and a base portion 106 supporting column 104. Robotic arm 102 is attached to the first end 104a of vertical column 104 and base portion 106 is attached to the second end 104b of vertical column 104. Base portion 106 may form three flanges 108, however, base portion 106 may form more than three flanges or fewer than three. Surgical robotic cart assembly 100 further includes at least three casters 110 with each caster being attached to a respective flange 108 of base portion 106.

With reference to FIGS. 1-4, cart 100 includes an immobilization assembly, shown generally as reference numeral 200 is attached to base portion 106. Immobilization assembly 200 includes a motor 202 having a first motor shaft 204 and a second motor shaft 206. Each first and second motor shaft 204, 206 may be configured to rotate in the same or opposite directions. Additionally, the immobilization assembly 200 includes a first cam housing 210 and a second cam housing 220. Each of the first and second cam housings 210, 220 are attached to the base portion 106.

Figure 3:
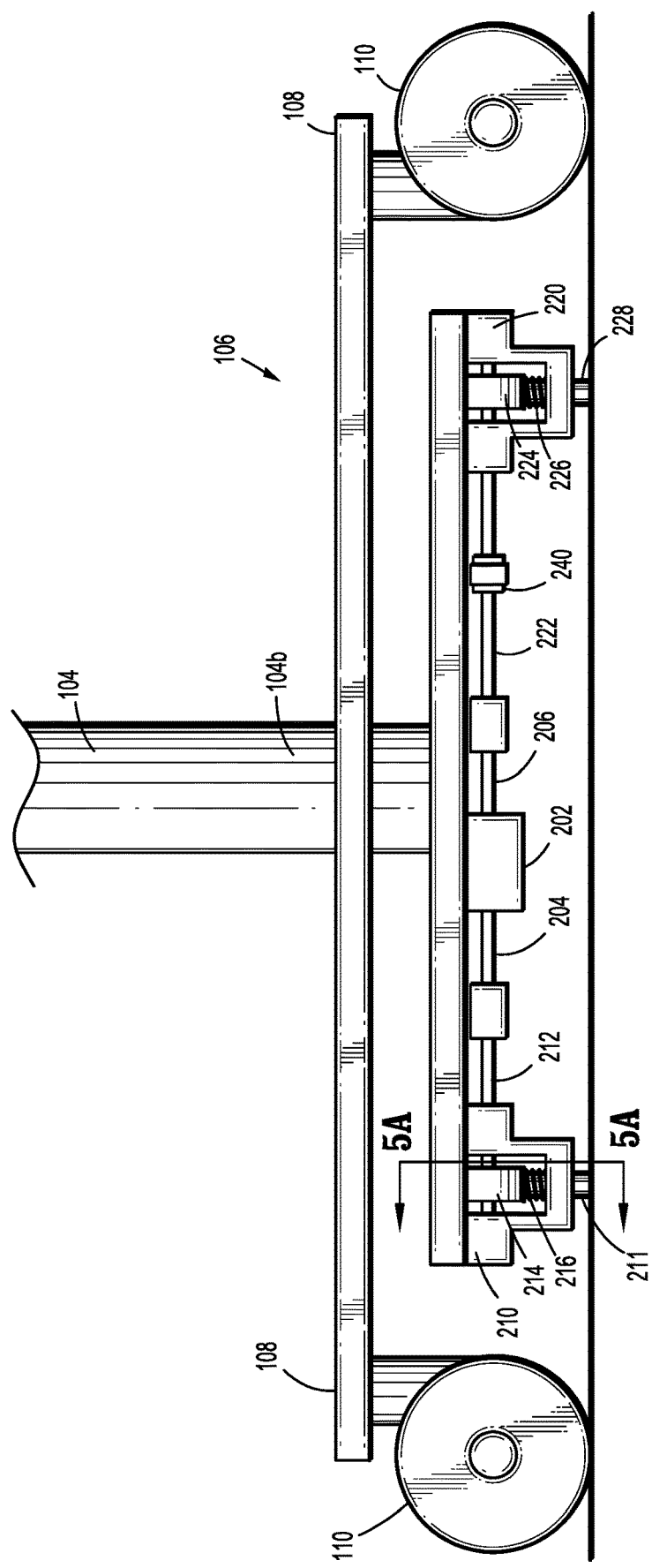
FIG. 3 is an plan, front view of the surgical robotic cart of FIG. 1 illustrating pistons thereof in a locked position.
Figure 4:
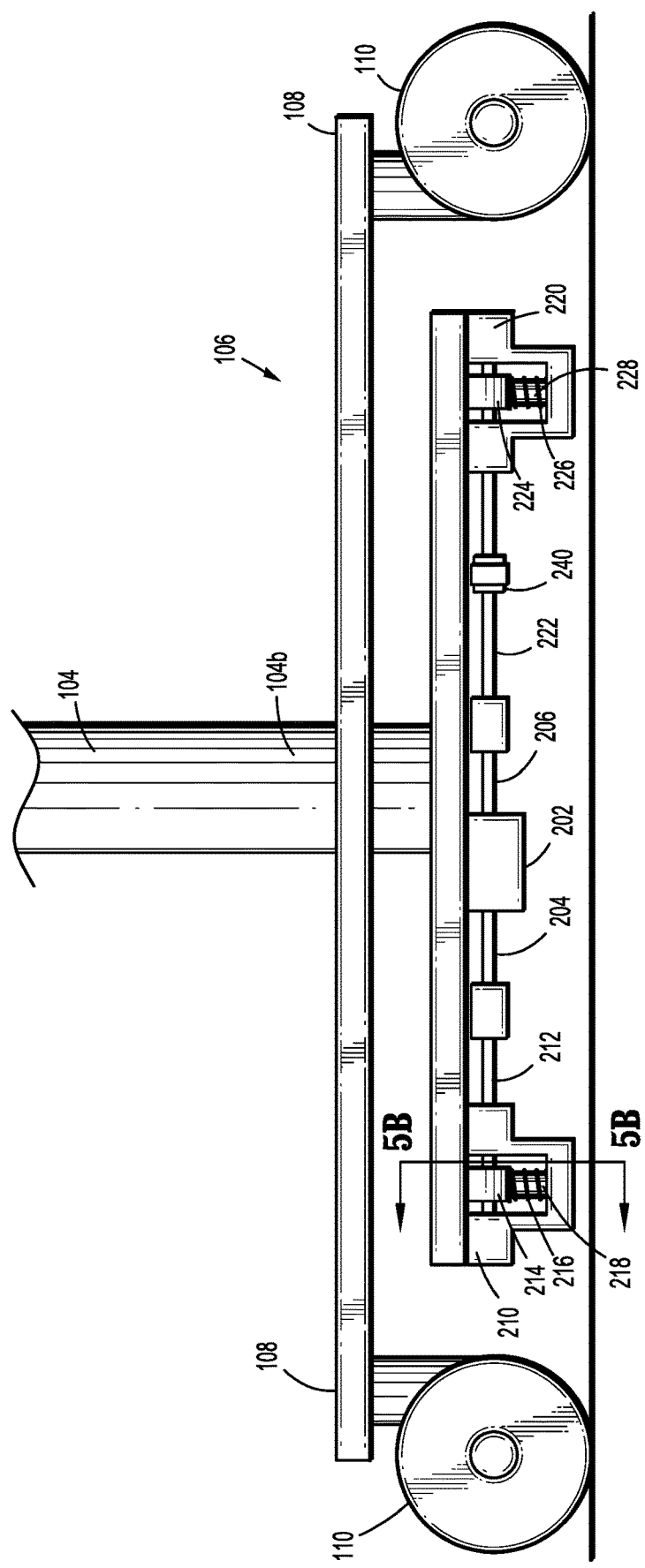
FIG. 4 is an plan, front view of the surgical robotic cart of FIG. 1 illustrating pistons thereof in an unlocked position.
Figure 5A:
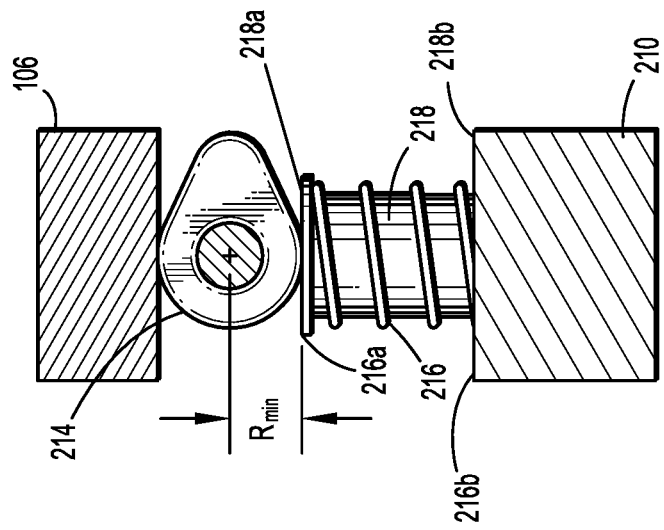
FIG. 5A is a side cross-sectional view of the immobilization assembly of FIGS. 1-3, taken along section line 5A-5A of FIG. 3, illustrating a cam engaging a piston to the locked position.
Figure 5B:
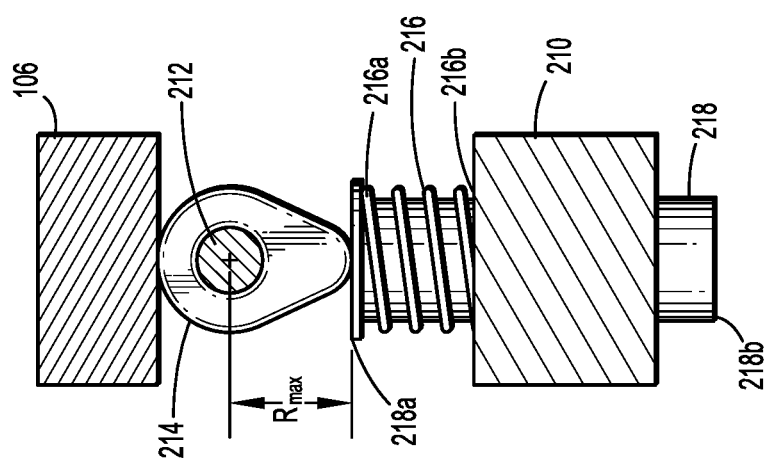
FIG. 5B is a side cross-sectional view of the immobilization assembly of FIGS. 1-4, taken along section line 5B-5B of FIG. 4, illustrating the cam engaging the piston to the unlocked position.

Immobilization assembly 200 further includes a first cam shaft 212 and a second cam shaft 222. Each of the first and second cam shafts 212, 222 are rotatably attached to a respective first cam housing 210 and second cam housing 220. Each of the first and second cam shafts 212, 222 may be attached to the respective first and second cam housing 210, 220 by a bearing or any other means permitting rotation of the first and second cam shafts 212, 222. Each of the first and second cam shafts 212, 222 support a respective first cam 214 and second cam 224. As seen in FIGS. 3 and 4, each first and second cam 214, 224 are disposed within a respective first and second cam housing 210, 220.

Each of the first and second cam shafts 212, 222 are respectively coupled to first and second motor shafts 204, 206. This may be achieved by using any type of rigid or fixed connection or coupling. Fixedly coupling first and second cam shafts 212, 222 to first and second motor shaft 204, 206 permits the torque from motor 202 to translate or be transmitted to the respective first and second cams 214, 224 of first and second cam shafts 212, 222.

Referring now to FIGS. 3-5B, each first and second cam housing 210, 220 includes a piston 218, 228 and spring 216, 226 arrangement. Each spring 216, 226 is configured to maintain each piston 218, 228 within its respective housing. In an embodiment, each spring, 216, 226 is a helical or coil spring, but any other suitable spring may be used. Each spring 216, 226 has a first end 216a, 226a and a second end 216b, 226b. The first end 216a, 226a of each spring is attached to a respective first end 218a, 228a of each piston 218, 228. The second end 216b, 226b of each spring 216, 226 is seated against the inside of the respective first and second cam housings 210, 220. Each first and second spring 216, 226 is disposed around a respective one of first and second pistons 218, 228.

Each first and second cam 214, 224 defines a lobe or eccentric shape where one portion of the cam 214, 224 has a minimum radius "$R_{min}$" and another portion of the cam 214, 224 has a maximum radius "$R_{max}$." The radius of the cam 214, 224 is measured from the center of the cam shaft 212, 222.

In operation, when motor 202 is activated, it rotates first and second motor shafts 204, 206. The rotational movement of first and second motor shafts 204, 206 is translated to rigidly or fixedly attached first and second cam shafts 212, 222. Since the first and second cams 214, 224 are fixedly attached to first and second cam shafts 212, 222, first and second cams 214, 224 simultaneously rotate with first and second cam shafts 212, 222.

When the portions of the first and second cams 214, 224 having the minimum radius "$R_{min}$" are engaging the respective first end 218', 228' of the first and second pistons 218, 228, the first and second pistons 218, 228 are maintained in or retracted within the respective cam housings 210, 220 by the force of springs 216, 226. When first and second cams 214, 224 are rotated such that the portions of the first and second cams 214, 224 having the maximum radius "$R_{max}$" is engaging the respective first end 218', 228' of the first and second pistons 218, 228 the torque transferred from motor 202 to first and second cams 214, 224 overcomes the resistive force of the respective springs 216, 226, thereby compressing springs 216, 226 and urging pistons 218, 228 out of the respective cam housings 210, 220, and extending pistons 218, 228 outwardly into a locked deployed or extended position. When the pistons 218, 228 are in the locked position, pistons 215, 228 contact the floor and immobilize the surgical robotic cart assembly by lifting the casters 110 out of contact with the floor.

Referring back to FIG. 2, immobilization assembly 200 may further include a third cam housing 230 and third cam shaft 232. Identical to first and second cam shafts 212, 222, third cam shaft 232 is rotatably attached to third cam housing 230 and forms a third cam (not shown) housed within third cam housing 230. Third cam housing 230 may also include a piston and spring (not shown) similar to the piston and spring of the first and second cam housing.

However, third cam shaft 232 is rigidly attached to a first sprocket 242, rather than a motor. First sprocket 242 may include a groove that seats a belt 244. Belt 244 is wrapped around first sprocket 242 and a second sprocket 240 that may also include a grove. Second sprocket 240 is rigidly coupled to second cam shaft 222 and belt 244 operatively couples first and second sprockets 242, 240. First and second sprockets 242, 240 may include any means to grippingly engage to belt 244. For example, first and second sprockets 242, 240 may define a plurality of teeth formed around a circumference of each of first and second sprockets 242, 240 adapted to interlock or mesh with a perforated belt. Belt 244 may be composed of a rubber or other appropriate material.

Also attached to base portion 106 of surgical robotic cart assembly 100 is a belt tensioner 246. Belt tensioner 246 may be disposed anywhere along belt 244. Belt tensioner 246 is configured to apply a pressure to belt 244 to make sure that belt 244 is securely fasted to first and second sprockets 242, 240. Belt tensioner 246 is adjustable in order to increase or decrease the tension in belt 244.

In operation, activation of motor 202 results in rotation of second cam shaft 222 and rigidly attached second sprocket 240. Since first and second sprockets 242, 240 are operatively connected via belt 244, when second sprocket 240 rotates, first sprocket 242 rotates. The torque applied to first sprocket 242 causes rigidly attached third cam shaft 232 to rotate thereby simultaneously rotating third cam (not shown) disposed within third cam housing 230. The rotation of the third cam causes third piston 238 of third cam housing 230 to move between an unlocked, retracted position to a locked, extended position.

In use, when motor 202 is activated in a first mode of operation, pistons 218, 228, 238 of the respective first, second, and third cam housings 210, 220, 230 simultaneously move between an unlocked, retracted position and a locked, extended position. Further in use, when motor 202 is activated in a second mode of operation, pistons 218, 228, 238 of the respective first, second, and third cam housings 210, 220, 230 simultaneously move between the locked, extended position and the unlocked, retracted position.

It is envisioned that motor 202 may be coupled to a power source that can be controlled by an operating console that is on surgical robotic cart assembly 100. Adapting motor 202 to be controlled via the operating console, allows the operator to easily control whether the cart is mobile or immobile.

Figure 6:
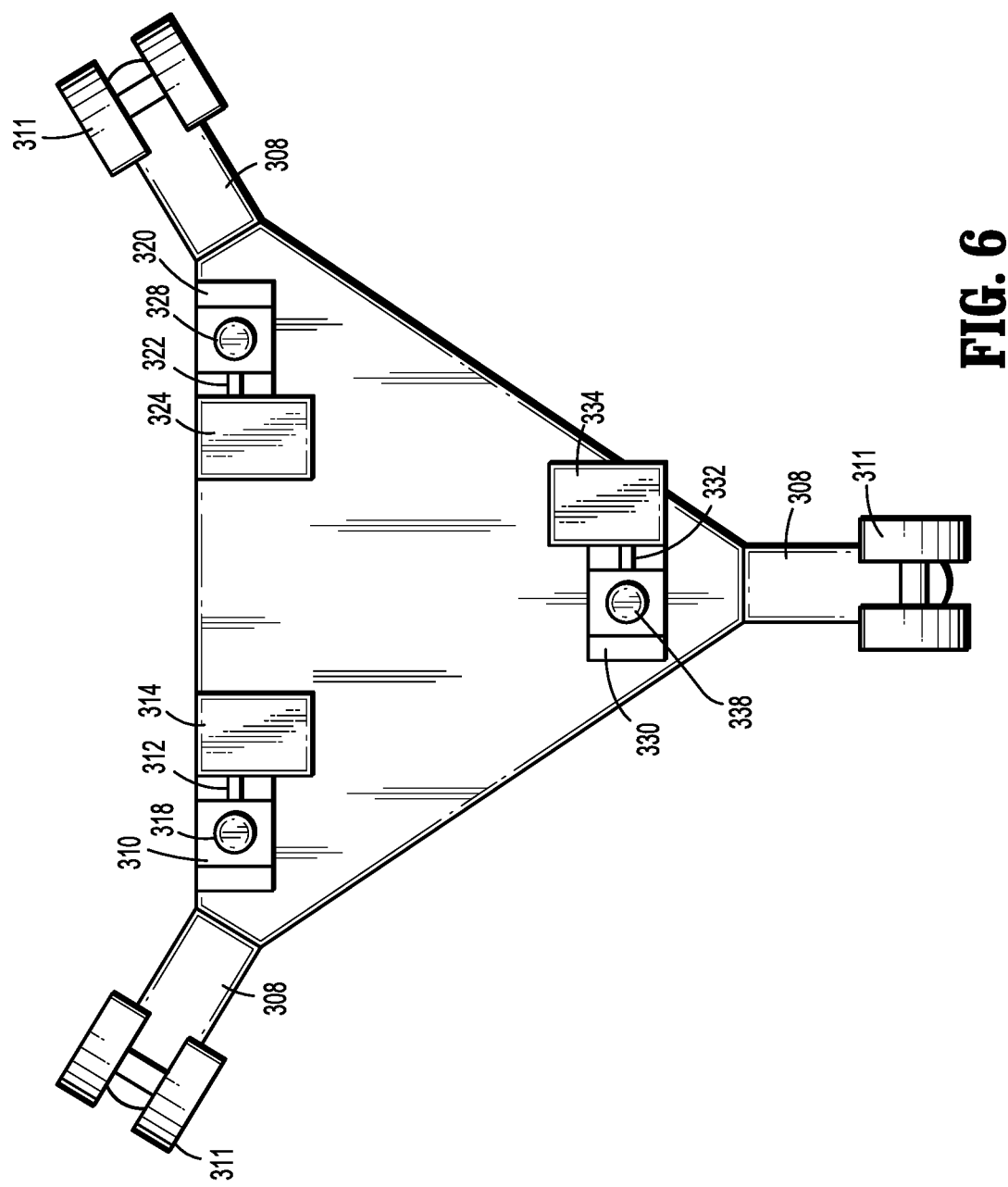
FIG. 6 is a plan, bottom view of an alternative embodiment of the surgical robotic cart of FIG. 1.

FIG. 6 shows an another exemplary embodiment of a surgical robotic cart assembly configured for use in accordance with the present disclosure having an alternative immobilization assembly generally identified by reference numeral 300. Immobilization assembly 300 is similar to immobilization assembly 200 except that each of the first, second, and third cam shafts 312, 322, 332 are coupled to a respective first, second, or third motor 314, 324, 334.

Immobilization assembly 300 includes first, second, and third motors 314, 324, 334. Each first, second, and third motor 314, 324, 334 is coupled to a respective first, second, and third cam shaft 312, 322, 332. Additionally, immobilization assembly 300 includes a first, second, and third cam housing 310, 320, 330. Similar to immobilization assembly 200, each of the first, second, and third cam shafts 312, 322, 332 form a respective first, second, and third cam, where each of the respective cams are disposed within a respective first, second, and third cam housing 310, 320, 330. Also, similar to immobilization assembly 200, each first, second, and third cam housings 310, 320, 330 of immobilization assembly 300 include a spring and piston that are configured to engage the respective first, second, and third cams of the first, second, and third cam shafts 312, 322, 332.

Each first, second, and third piston 318, 328, 338 are configured to move independently. It is beneficial to configure each first, second, and third piston 318, 328, 338 to be independently operated to level the robotic arm if the surgical robotic cart assembly is on an uneven surface or an incline. Further, moving only one of the pistons into the locked position allows the surgical robotic cart to pivot about the piston in the locked position. This is beneficial because it allows for proper orientation of the surgical robotic cart assembly. The surgical robotic cart assembly may further include a leveling mechanism (not shown). The level may be either a digital level, spirit level, or any other suitable mechanism.

Figure 7:
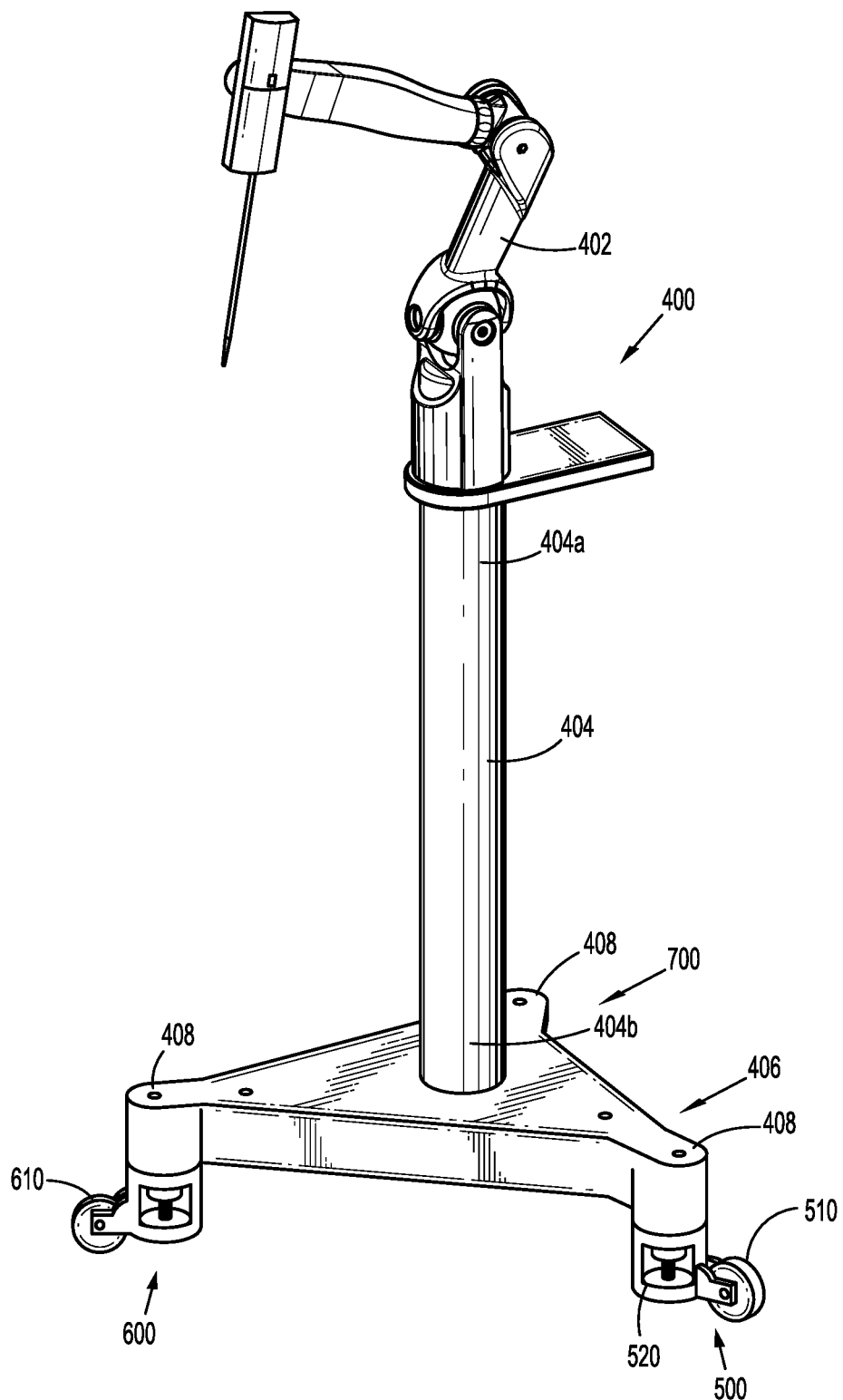
FIG. 7 is a perspective view of an alternative embodiment of a surgical robotic cart having an immobilization assembly in accordance with the present disclosure.

Turning to FIG. 7, another exemplary embodiment of a surgical robotic cart assembly configured for use in accordance with the present disclosure is shown generally identified by reference numeral 400, although it is also envisioned that the aspects and features of the present disclosure be similarly incorporated into any suitable surgical robotic cart assembly. Surgical robotic cart assembly 400 generally includes a robotic arm 402, a vertical column 404 having a first end 404a and a second end 404b and a base portion 406 supporting column 404. Robotic arm 402 is attached to the first end 404a of vertical column 404 and base portion 406 is attached to the second end 404b of vertical column 404. Base portion 406 may form three flanges 408, however, base portion 406 may form more than three flanges or fewer than three flanges. Surgical robotic cart assembly 400 further includes at least three immobilization assemblies generally shown as reference numeral 500, 600, 700. Each immobilization assembly 500, 600, 700 is attached to each of the flanges 408 of base portion 406.

Figure 8:
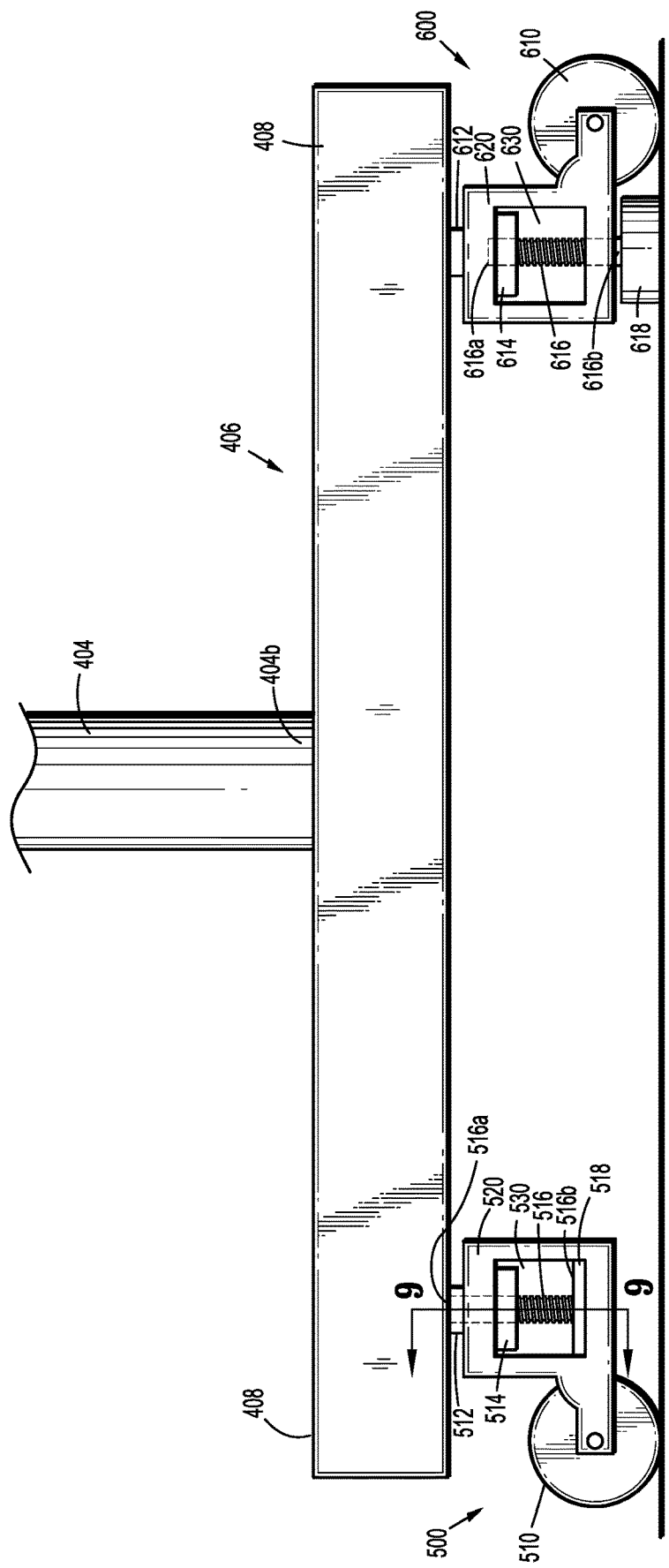
FIG. 8 is an plan, front view of the surgical robotic cart of FIG. 7 illustrating one piston in a locked position and another piston in an unlocked position.
Figure 9:
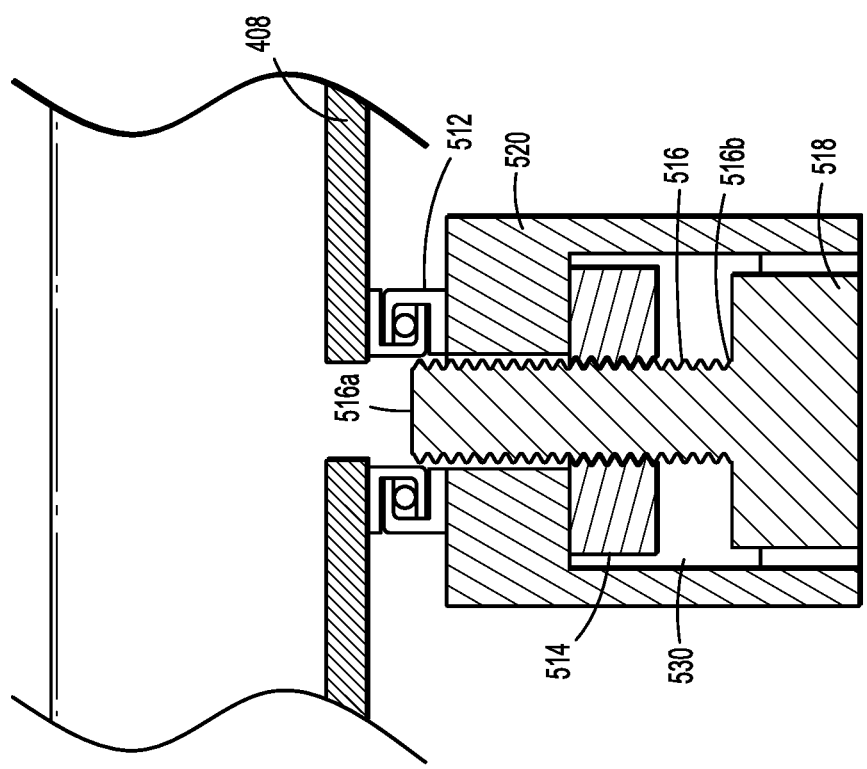
FIG. 9 is a side cross-sectional view of the immobilization assembly of FIGS. 7 and 8, taken along section line 9-9 of FIG. 8, illustrating one piston, disposed within a housing of a caster, in the unlocked position.

With reference to FIGS. 7-9, in the interest of brevity, immobilization assembly 500 will be discussed, however, immobilization assembly 500 is identical to immobilization assemblies 600 and 700. The following exemplary discussion of the operation of immobilization assembly 500 is the same or substantially similar for immobilization assemblies 600 and 700.

With reference to FIGS. 8 and 9, immobilization assembly 500 includes a caster 510 pivotally attached to housing 520. Housing 520 is rotatably attached to flange 408. This may be achieved by using a swivel bearing 512, or any other appropriate means. Housing 520 may be cylindrical in shape defining a hollow core or center. Housing 520 further includes at least one window 530. Disposed within housing 520 is a threaded shaft 516 having a first end 516a and a second end 516b. Disposed on the second end 516b of the threaded shaft 516 is a foot 518. Rotatably coupled to housing 520 is a knob 514. Knob 514 is threadingly engaged to threaded shaft 516. Any type of knob including, but not limited to, a star knob or a wing nut may be used.

With reference to FIG. 9, in use, rotating knob 514 (e.g., manually) in a first direction translates threaded shaft 516 into an unlocked position where foot 518 is retracted into housing 520. Further, rotating knob 514 in a second direction, opposite the first direction, translates threaded shaft 516 into a locked position where foot 518 is extended outside housing 520 and is engaging the floor. In an embodiment, foot 518 is extended by an amount sufficient such that immobilization assembly 500 may lift the caster 510, and in turn the cart, from the floor.

When each of the immobilization assemblies 500, 600, 700 are in the locked position, the surgical robotic cart assembly is immobile. Each immobilization assembly 500, 600, 700 may be operated independently as to allow the surgical robotic cart assembly to operate on an uneven surface. Since each of the immobilization assemblies 500, 600, 700 may be independently set to a locked or unlocked position, if one immobilization assembly is in the locked position while the other two immobilization assemblies are in the unlocked position, the surgical robotic cart assembly is able to pivot about the one locked immobilization assembly. Further, surgical robotic cart assembly 400 may include a digital level, spirit level or any other appropriate level.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the claimed invention. Therefore, the above description should not be construed as limiting, but merely as exemplifications of particular embodiments. Those skilled in the art will envision other modifications within the scope and spirit of the claims appended hereto.

What is claimed is:
1. A surgical robotic cart assembly, including:
   a vertical column supporting a robotic arm thereon;
   a base portion secured to the vertical column;
   casters attached to the base portion and adapted to allow the surgical robotic assembly to move; and
   an immobilization assembly coupled to the base portion, the immobilization assembly having at least two pistons configured to move between an unlocked position and a locked position, wherein when the at least two pistons are in the unlocked position the surgical robotic cart assembly is mobile, and wherein when the at least two pistons are in the locked position and in contact with a floor on which the cart assembly is supported, the cart assembly is immobile, wherein the immobilization assembly further includes:
      a motor having a first motor shaft and a second motor shaft operatively coupled to the base portion;
      a first cam shaft supporting a first cam and a second cam shaft supporting a second cam, the first and second cam shafts coupled to a respective one of the first and second motor shafts; and a first cam housing and a second cam housing each attached to the base portion, the first and second cam housings rotatably coupled to a respective one of the first and second cam shafts.

2. The surgical robotic cart assembly of claim 1, wherein the first and second cams are disposed within a respective first and second cam housing.

3. The surgical robotic cart assembly of claim 2, wherein each of the first and second cam housings include a piston of the at least two pistons, each piston coupled to a spring disposed around a circumference of the piston and configured to hold the piston in the unlocked position.

4. The surgical robotic cart assembly of claim 3, wherein each of the first and second cams of the first and second cam shafts have a lobe shape defining a minimum radius and a maximum radius that is greater than the minimum radius.

5. The surgical robotic cart assembly of claim 4, wherein at least a portion the first and second cams are configured to engage a respective piston and spring of the first and second cam housings, wherein when the at least one portion of the first and second cams having the minimum radius engages the respective piston of the first and second cam housings, the pistons are in the unlocked position and the springs are in a released and uncompressed position.

6. The surgical robotic cart assembly of claim 5, wherein when the at least one portion of the first and second cams having the maximum radius engages the respective pistons of the first and second cam housings, the pistons are in the locked position and the springs are in a compressed position.

7. The surgical robotic cart assembly of claim 1, wherein the immobilization assembly further includes a third cam shaft, wherein the third cam shaft is rotatably coupled to a third cam housing attached to the base portion, the third cam housing including a respective piston fixed to a respective spring, the spring of the third cam housing disposed around a circumference of the piston of the third cam housing and configured to hold the piston thereof in an unlocked position, and wherein at least one of the first or second cam shafts is operatively coupled to a third cam shaft.

8. The surgical robotic cart assembly of claim 7, wherein the third cam shaft supports a third cam having a lobe shape defining a minimum radius and a maximum radius greater than the minimum radius.

9. The surgical robotic cart assembly of claim 8, wherein at least a portion of the third cam is configured to engage the piston and spring of the third cam housing, wherein when the at least one portion of the third cam having the minimum radius engages the piston of the third cam housing, the respective piston is in the unlocked position and the respective spring is in a released and uncompressed position.

10. The surgical robotic cart assembly of claim 9, wherein when the at least one portion of the third cam engaging the piston and spring of the third cam housing has the maximum radius, the piston is in the locked position and the spring is in a compressed position.

11. The surgical robotic cart assembly of claim 7, further comprising a belt operatively coupling the third cam shaft to at least one of the first or second cam shafts.

12. The surgical robotic cart assembly of claim 11, further including a belt tensioner attached to the base portion, the belt tensioner configured to apply a pressure to the belt to increase a tension thereof.

13. A surgical robotic cart assembly, including:
a vertical column supporting a robotic arm thereon;
a base portion secured to the vertical column;
casters attached to the base portion and adapted to allow the surgical robotic assembly to move; and
an immobilization assembly coupled to the base portion, the immobilization assembly having at least three pistons configured to move between an unlocked position and a locked position, wherein when the at least three pistons are in the unlocked position the surgical robotic cart assembly is mobile, and wherein when the at least three pistons are in the locked position and in contact with a floor on which the cart assembly is supported, the cart assembly is immobile, wherein the immobilization assembly further includes:
first, second, and third motors;
a first cam shaft supporting a first cam, a second cam shaft supporting a second cam, a third cam shaft supporting a third cam, the first, second, and third cam shafts coupled to a respective one of the first, second, and third motors; and
a first cam housing, a second cam housing, and a third cam housing each attached to the base portion, the first, second, and third cam housings rotatably coupled to a respective one of the first, second, and third cam shafts.

14. The surgical robotic cart assembly of claim 13, wherein the first, second, and third cams are disposed within a respective one of the first, second, and third cam housings.

15. The surgical robotic cart assembly of claim 14, wherein each of the first, second, and third cam housings include a piston of the at least three pistons, each piston coupled to a spring disposed around a circumference of the piston and configured to hold the piston in the unlocked position.

16. The surgical robotic cart assembly of claim 15, wherein each of the first, second, and third cams of the first, second, and third cam shafts have a lobe shape defining a minimum radius and a maximum radius that is greater than the minimum radius.

17. The surgical robotic cart assembly of claim 16, wherein at least a portion the first, second, and third cams are configured to engage a respective piston and spring of the first, second, and third cam housings, wherein when the at least one portion of the first, second, and third cams having the minimum radius engages the respective piston of the first, second, and third cam housings the pistons are in the unlocked position and the springs are in a released and uncompressed position.

18. The surgical robotic cart assembly of claim 17, wherein when the at least one portion of the first, second, and third cams having the maximum radius engages the respective pistons of the first, second, and third cam housings, the pistons are in the locked position and the springs are in a compressed position.

19. A surgical robotic cart assembly, including:
a vertical column;
a robotic arm supported on the vertical column;
a base portion supporting the vertical column;
casters attached to the base portion and adapted to allow the surgical robotic assembly to move; and
an immobilization assembly coupled to the base portion, the immobilization assembly having at least two pistons configured to move between an unlocked position and a locked position, wherein when the at least two pistons are in the unlocked position the surgical robotic cart assembly is mobile, and wherein when the at least two pistons are in the locked position and in contact with a floor on which the cart assembly is supported, the cart assembly is immobile, wherein the immobilization assembly further includes:

a motor having a first motor shaft and a second motor shaft operatively coupled to the base portion;

a first cam shaft supporting a first cam and a second cam shaft supporting a second cam, the first and second cam shafts coupled to a respective one of the first and second motor shafts; and a first cam housing and a second cam housing each attached to the base portion, the first and second cam housings rotatably coupled to a respective one of the first and second cam shafts.

* * * * *